(12) United States Patent
Keyworth

(10) Patent No.: US 9,784,716 B2
(45) Date of Patent: Oct. 10, 2017

(54) SCANNING METHOD AND APPARATUS

(71) Applicant: Flexlife Limited, Aberdeen (GB)

(72) Inventor: Craig Keyworth, Aberdeen (GB)

(73) Assignee: Flexlife Limited, Aberdeen (GB)

( * ) Notice: Subject to any disclaimer, the term of this patent is extended or adjusted under 35 U.S.C. 154(b) by 502 days.

(21) Appl. No.: 14/350,279

(22) PCT Filed: Oct. 5, 2012

(86) PCT No.: PCT/GB2012/052484
§ 371 (c)(1),
(2) Date: Apr. 7, 2014

(87) PCT Pub. No.: WO2013/050786
PCT Pub. Date: Apr. 11, 2013

(65) Prior Publication Data
US 2014/0238137 A1  Aug. 28, 2014

(30) Foreign Application Priority Data
Oct. 5, 2011  (GB) .................................. 1117174.1

(51) Int. Cl.
*G01N 29/04* (2006.01)
*G01M 3/00* (2006.01)

(52) U.S. Cl.
CPC .............. *G01N 29/04* (2013.01); *G01M 3/00* (2013.01); *G01N 29/043* (2013.01); *G01N 2291/044* (2013.01); *G01N 2291/2634* (2013.01)

(58) Field of Classification Search
CPC .................................................... G01N 29/04
See application file for complete search history.

(56) References Cited

U.S. PATENT DOCUMENTS 3,228,233 A    1/1966 Keldenich
4,487,072 A *  12/1984 Livingston ............. G01N 29/07
                                                        73/622
(Continued)

FOREIGN PATENT DOCUMENTS

CA    2545285 A1    5/2005
EP    0415848 A1    3/1991
(Continued)

OTHER PUBLICATIONS

Berke, Michael. Nondestructive Material Testing with Ultrasonics. Sep. 2000. Issue 5 vol. 9. http://www.ndt.net/article/v05n09/berke/berke1.htm.*

(Continued)

*Primary Examiner* — Paul West
*Assistant Examiner* — Mark A Shabman
(74) *Attorney, Agent, or Firm* — Winstead PC

(57) ABSTRACT

A method of assessing the condition of a tubular member comprises driving an ultrasonic probe to fire a short pulse ultrasonic beam at the outer surface of the tubular member and analyzing the reflected signals from the tubular member to assess the condition of the tubular member. The apparatus comprises an ultrasonic probe (22), means for driving the probe to fire a short pulse ultrasonic beam at the outer surface of the tubular member and means for converting the reflected ultrasonic beam into image signals which can be analyzed to assess the condition of the tubular member.

17 Claims, 3 Drawing Sheets

(56) References Cited

U.S. PATENT DOCUMENTS

| | | | |
|---|---|---|---|
| 4,522,064 A | | 6/1985 | McMillan |
| 4,541,064 A | | 9/1985 | Livingston |
| 4,625,557 A | * | 12/1986 | Rutherford .......... G01N 29/265 |
| | | | 73/635 |
| 5,052,394 A | * | 10/1991 | Carpenter ........... G01S 7/52049 |
| | | | 600/442 |
| 5,389,848 A | * | 2/1995 | Trzaskos ............... B06B 1/0611 |
| | | | 310/322 |
| 5,535,628 A | * | 7/1996 | Rutherford .......... G01N 29/225 |
| | | | 73/622 |
| 5,804,730 A | | 9/1998 | Pfannenstiel et al. |
| 6,536,283 B1 | | 3/2003 | Hatley |
| 2010/0275694 A1 | | 11/2010 | Roberts |

FOREIGN PATENT DOCUMENTS

| | | |
|---|---|---|
| GB | 2446670 A | 1/2009 |
| GB | 2462078 A | 1/2010 |
| GB | 2475337 A | 5/2011 |

OTHER PUBLICATIONS

Filipas, Alin, "International Search Report," prepared for PCT/GB2012/052484, dated Jan. 7, 2013, 6 pages.

\* cited by examiner

SCANNING METHOD AND APPARATUS

This invention relates to a scanning method and apparatus and more specifically relates to a method and apparatus for scanning a tubular member and more particularly a pipeline, using ultrasonic technology to collect information on the integrity of the pipeline.

Pipes are typically described as rigid or flexible. Flexible Pipe is a term used to describe a multi-layered pipe, which is formed from materials which allow it to bend relatively easily. It is generally constructed of various layers of materials such as polymers and metals or composites.

Flexible pipes are used throughout the oil and gas industry both onshore, and predominately offshore. Their attraction is the ease of installation and their ability to withstand cyclic bending, and therefore they are less prone to fatigue than rigid risers.

FIGS. 1 and 2 show part cross-sections through two typical flexible pipe constructions.

The flexible pipe of FIG. 1 is a rough bore flexible pipe, which comprises an inner carcass 1 generally formed of interlocked wires, which provides stability to the pipeline and resists collapse of the construction. Surrounding the carcass is a pressure sheath 2, which is generally formed by a thermoplastic inner fluid barrier and provides a seal to prevent internal fluid flowing in the pipeline from escaping from the inner carcass.

A pressure armour 3 is formed around the outer surface of the pressure sheath and provides hoop strength to the pipeline to prevent collapse.

A helically wound tensile armour 4 formed of rectangular or round wire or composite rods is provided over the pressure armour to provide axial support and to support the hoop strength of the pipeline. A wear layer 5 of thermoplastic or tape overlies the tensile armour 4 and limits the steel layer wear by reducing the contact forces and abrasion thereon. The wear layer 5 also constrains the wires and acts as a manufacturing aid.

In the example shown, a further tensile armour 4' is applied over the wear layer 5 and followed by a thermal insulation layer 6 which reduces heat loss from the pipeline. An outer sheath 7 of between 3 and 30 mm thickness surrounds the inner layers, said outer sheath being formed of a thermoplastic, which provides environmental protection and prevents seawater ingress into the pipeline.

FIG. 2 shows a typical construction for a smoothbore flexible pipe which is formed of an inner liner 8 of thermoplastics, which provides an inner fluid barrier without the requirement for an internal carcass, surrounded by a pressure armour 3 as described in relation to FIG. 1. Surrounding the pressure armour 3 is an intermediate seal 9, which is formed from a thermoplastic hydrostatic pressure barrier, which allows the pressure armour 3 to resist hydrostatic load when the outer sheath 7 is breached as discussed further below.

A tensile armour 4 surrounds the intermediate seal over which a wear layer 5 and further tensile armour 4' are provided. Finally the outer sheath 7 surrounds the preceding layers as described above.

In some cases, a further thermoplastic extrusion (not shown) may be provided over the outer sheath 7 to protect the outer sheath 7 from loads and abrasion and an external carcass (not shown) may surround the entire pipeline to protect the sheath 7 from loads, abrasion and impact damage, particularly where the pipeline is laid on the sea bed.

Flexible pipes are usually constructed using the layers listed above and can comprise multiples of these layers depending on the application The annulus of the pipe, the pressure armour 3 and tensile armour 4, 4' layers are of particular interest in relation to the present invention. The annulus is the space between the outer sheath 7 and an internal sealing layer such as the internal pressure sheath 2, 3, liner, or intermediate seal 9. The tensile and pressure armour layers are the outer wires, which withstand as their name suggests the tensile loads and pressure induced loads of the pipe and are located within the annulus.

The fatigue resistance of a flexible pipe is significantly reduced when the tensile armour 4, 4' or pressure armour 3 wires of a pipe are exposed to seawater, corroded, or damaged.

In each flexible pipe configuration, the flexible pipe annulus condition is critical to the service life and performance of the pipe. This becomes more important the more dynamic the pipe. Typically, Risers and Dynamic Jumpers are much more sensitive to fatigue than Flowlines and Static Jumpers.

The annulus can be flooded through either seawater ingress or permeated fluid from the bore. In either case this environment reduces the design service life of the pipe. Assessing and monitoring this condition particularly in relation to the level of flooding in the annulus, i.e. either the height of fluid present in the annulus or the ration of flooded to non flooder sections of the pipe, is therefore a key factor in prediction of service life and assessment of flexible pipe assets offshore. Failure to monitor the annulus environment can lead to loss of containment of the pipe's contents and cause serious environmental damage, injury, fatality, or even total loss of the offshore platform to which the flexible pipe is connected. Flooding can occur either throughout the entire pipeline or alternatively in localised pockets along the pipeline.

GB2446670B describes a method of monitoring the integrity of a flexible pipeline by scanning the pipeline with an ultrasonic scanner to identify the level of flooding within the pipeline.

This enables an operator to assess the condition of the pipeline along its scanned length and particularly to identify any flooded regions within the annulus by identifying the interface between a fluid filled annulus and one with no fluid present from the change in the reflected signal across the interface. Therefore individual flooded areas along the length of the pipeline can be identified and the level or extent of flooding in the pipeline determined by scanning the pipeline externally without having to resort to invasive techniques which require the pipeline to be drained of fluids and a probe or other tool introduced pushed or pulled through the pipeline which requires significant effort and cost in relation to equipment, manpower and downtime in production of hydrocarbons through the pipeline.

Whilst the method described in this document goes some way to providing a solution to the problem of assessing the condition of the annulus of a flexible riser without using invasive techniques, it is possible that the accuracy of the results can be effected by the amount of reverberation generated when the ultrasonic beam is fired at the pipe. Typically the driving voltage of the ultrasonic beam has been in the region of around 100 volts with frequencies of around 2 to 10 MHz and the magnitude of the return signal could in some cases be low.

Therefore it is an aim of the present invention to provide an improved method of assessing the condition of a flexible riser and particularly of enhancing the return signal of the scanning process.

Furthermore, the present invention aims to provide an improved apparatus for assessing the condition of the annulus of a flexible riser.

According to one aspect of the present invention there is provided a method of assessing the condition of a tubular member, the method comprising driving an ultrasonic probe to fire a short pulse ultrasonic beam at the outer surface of the tubular member and analysing the reflected signals from the tubular member to assess the condition of the tubular member.

In some embodiments the tubular member is a flexible riser. Preferably the method further includes the step of analysing the reflected signals to identify corrosion in the armour wires of the flexible riser. Preferably also the method includes the step of identifying the front and back walls of the armour wires.

Alternatively or additionally the method of analysing the reflected signals includes the step of identifying an interface between areas in the annulus of the riser which are flooded and those which are not.

Preferably the probe has a front face diameter of between 9 and 12 mm. Preferably also the probe comprises polyvinylidenefluoride (PVDF).

Preferably also the probe is driven at a voltage of around 700V to 1 Kv. Preferably also the probe fires pulses of between 4 and 6 Mhz with a focal length of between 5 and 100 mm. By driving the probe with such a high voltage and firing a short pulse ultrasonic beam at the tubular member and by matching the natural frequencies and/or mechanical behaviours of the materials of the probe and the outer sheath of the riser, the losses in signal strength and quality are at least reduced or significantly improved thus ensuring that a strong return signal is generated.

Preferably the method further comprises the step of mounting the probe adjacent to the outer surface of the tubular member.

Advantageously the method further comprises the step of moving the probe relative to the tubular member and preferably traversing the probe along a path parallel to the longitudinal axis of the tubular member and or radially around the riser to perform a scanning operation along selected sections or lengths of the tubular member.

Preferably the probe is mounted on a frame and the frame is mounted to or around the tubular member to facilitate mounting the probe adjacent to the outer surface of the tubular member.

Advantageously the frame is driven along the riser to move the probe relative to the tubular member.

Conveniently the frame is launched on an ROV and operated remotely to attach to and/or traverse along the tubular member.

Preferably also the method comprises the further step of centering the probe on the tubular member. More preferably the method comprises the step of providing multiple probes and driving the multiple probes to fire short pulse ultrasonic beams at the surface of the tubular member. Preferably also the multiple probes are aligned in pairs mounted diametrically oppositely within the frame. Preferably also at least two such pairs of probes are provided mounted substantially at 90 degree angles around the frame such that the, the probes being positionally adjustable to maintain the intersection between the two ultrasonic beams at the centre of the riser thereby providing a self centering option for the probes around the tubular member.

The present invention provides a method of assessing the condition of a tubular member and particularly a flexible riser and particularly the integrity of the annulus of the riser.

Furthermore, the present invention also provides a method of ongoing monitoring of the condition of the tubular member which allows the operator to take preventative measures before the condition of the riser reaches a critical level which could lead to failure of the tubular member.

According to a further aspect of the present invention there is provided an apparatus for assessing the condition of a tubular member, the apparatus comprising an ultrasonic probe, means for driving the probe to fire a short pulse ultrasonic beam at the outer surface of the tubular member and means for converting the reflected ultrasonic beam into image signals which can be analysed to assess the condition of the tubular member.

Preferably the apparatus further comprises means for displaying the image signals.

Preferably the probe is adapted to be driven at a voltage of around 700V to 1 Kv. Preferably also the probe fires pulses of between 4 and 6 MHz with a focal length of between 5 and 100 mm. It will be appreciated by an appropriately skilled person that such pulse lengths would be classed as short pulse ultrasound.

By driving the probe at such voltages this provides improved power for the ultrasonic beam to penetrate the multiple layers found particularly in the complex structure of a flexible pipe. By improving the power of the ultrasonic beam, the magnitude of the reflected signals is increased and the accuracy of the resulting information that can be analysed to determine the condition of the annulus of the flexible pipe is also greatly improved.

Preferably the apparatus further comprises a frame adapted to be mounted adjacent to or around the outer surface of a tubular member.

Conveniently the ultrasonic probe is mounted upon the frame in an orientation perpendicular to the longitudinal axis of the frame.

Advantageously means are provided for moving the frame relative to the tubular member. Most preferably driving means are provided for moving the frame along or across the outer surface of the tubular member.

Preferably the apparatus further comprises a plurality of probes and more preferably a pair of probes mounted in the frame in opposing diametric alignment.

Conveniently a second pair of probes is provided perpendicularly to the first pair such that the longitudinal axes of the two pairs of probes cross within the flexible riser when the frame is mounted on a tubular member and the ultrasonic beams fired by the probes converge on the centre of the tubular member.

Conveniently the frame comprises a hinged collar which can open to allow the frame to be mounted around a tubular member. Advantageously a pair of collars are provided, one at either end of the frame.

Advantageously an umbilical is provided between the probe or probes and the display device.

Preferably the probe has a front face diameter of between 9 and 12 mm.

Preferably also the probe is constructed with polyvinylidenefluoride (PVDF).

Advantageously means are provided on the frame for moving the probe or probes vertically and/or horizontally over the surface of the tubular member.

An embodiment of the present invention will now be described with reference to the enclosed Figures in which.

Figure 1:
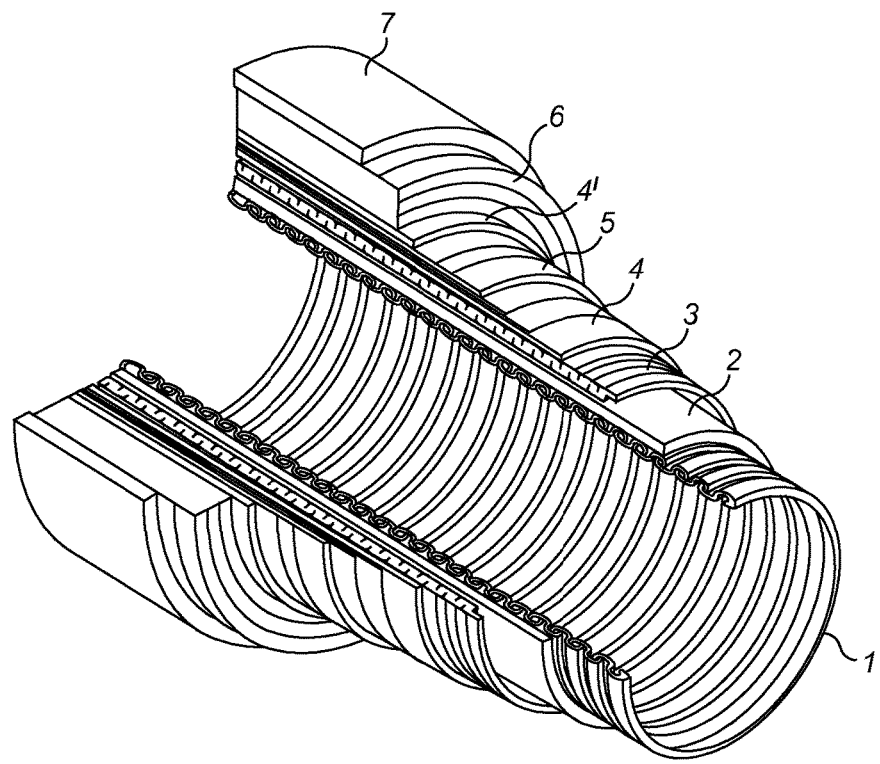
FIG. 1 is a schematic part sectional view of a first form of flexible riser.
Figure 2:
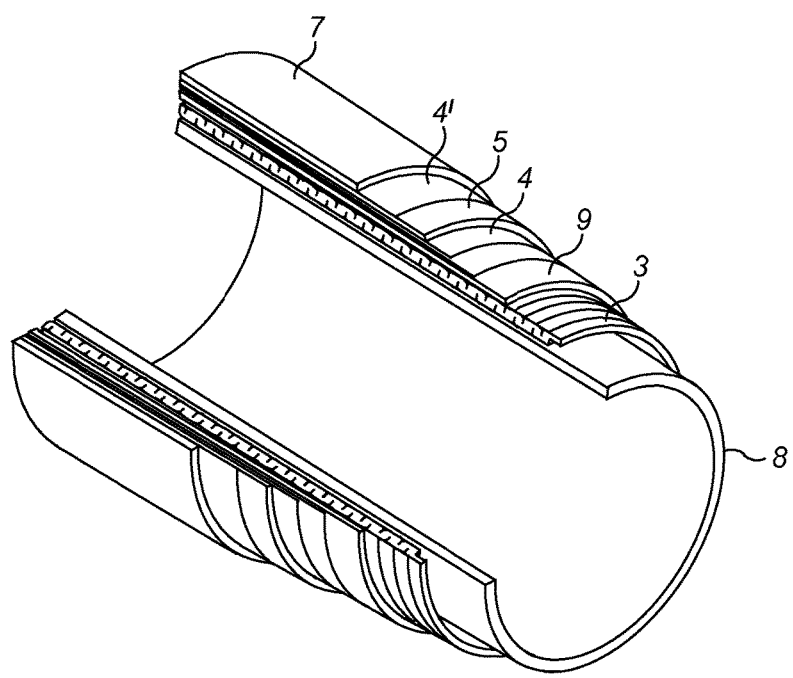
FIG. 2 is a further schematic part sectional view of a second form of flexible riser.
Figure 3:
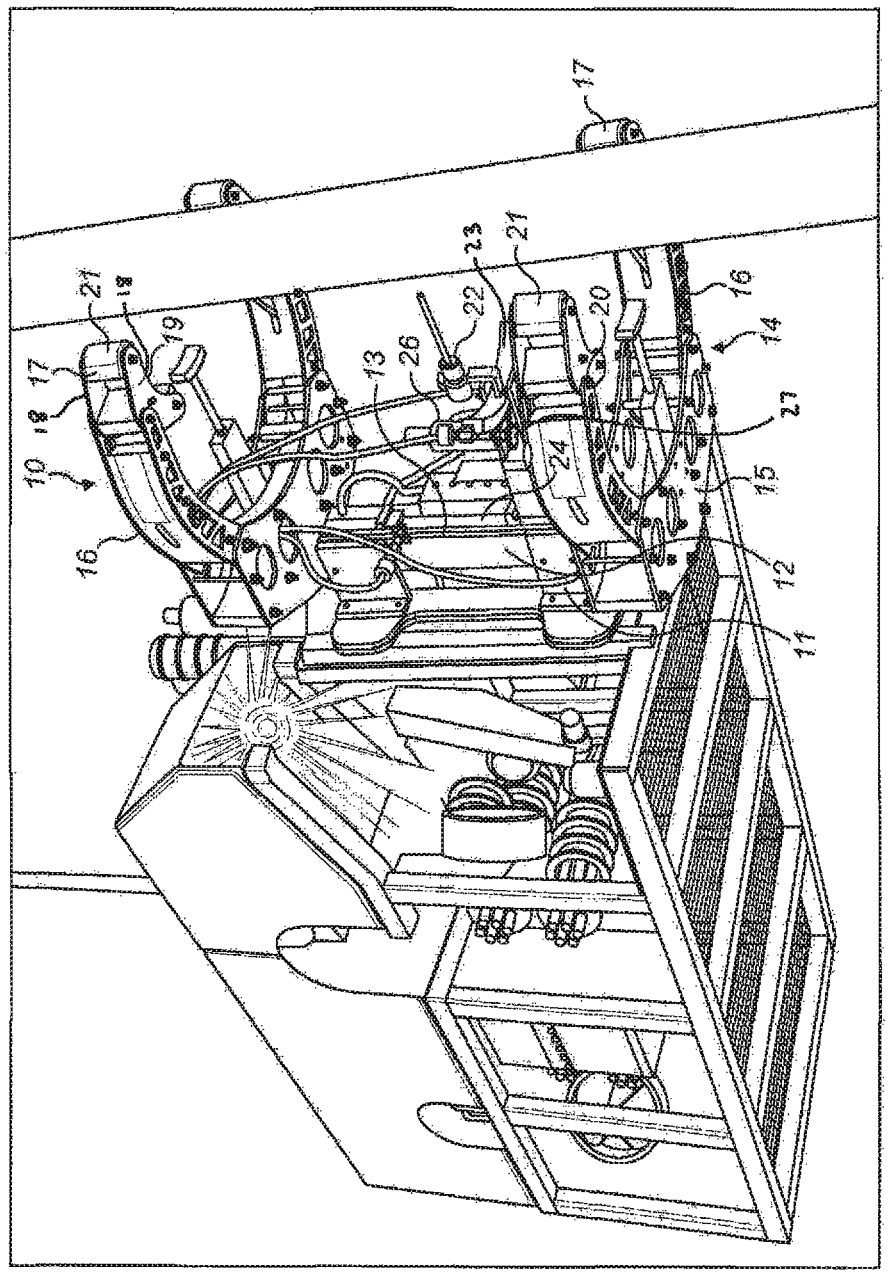
FIGS. 3 and 4 are schematic perspective views of an apparatus for assessing the condition of a tubular member such as a flexible riser shown in FIG. 1 or 2, according to one aspect of the present invention.
Figure 4:
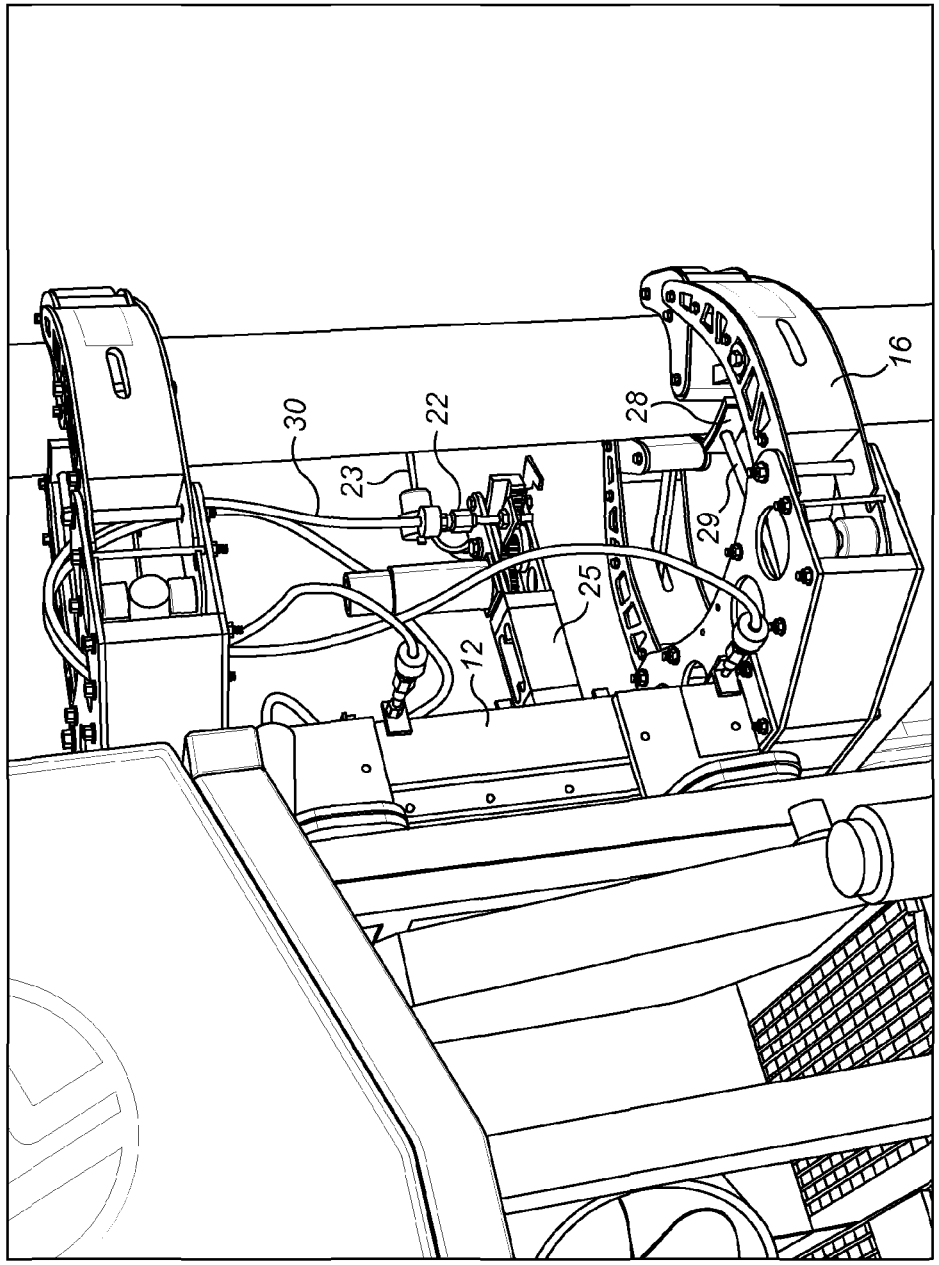

Turning now to the figures, FIG. 3 shows an inspection apparatus 10 comprising a frame 11 which is adapted to be mounted around the outer surface of a tubular member such as a flexible riser as shown. The frame comprises a substantially rectangular U-shaped channel member 12 which is open along the upper surface 13. A collar 14 is mounted on either end of the channel member, the collar comprising a rear portion 15 mounted to the upper and lower ends of the channel member and a pair of arms 16 which extend from either end of the rear portion and can be pivotally moved between a first position in which the arms are in an open position and a second closed position in which the arms are moved towards each other to grip onto a flexible riser when the frame is placed adjacent to the riser.

Gripping means 17 are provided at the free end of each arm for gripping a riser. The gripping means comprise upper and lower plates 18 which are generally L-shaped with a curved front face 19. The plates are mounted to the ends of the arms through a pivot pin 20 at the junction of the legs of the plates. Rollers 21 are provided between the upper and lower plates serving to grip the outer surface of the riser.

The collars are shown as being at the upper and lower ends of the channel member in this embodiment although they could of course be provided at any position and in any number(s) along the frame.

An ultrasonic probe 22 is mounted on the frame. The probe is fixed to a curved mounting plate 23. Means are provided for adjusting the position of the plate within the frame, and thereby the position of the probe within the frame. In this embodiment a hydraulic cylinder 24 is mounted within the open channel member of the frame and the plate is mounted to an arm 25 extending laterally from the hydraulic cylinder towards the open ends of the arms of the collars. Thus as the hydraulic cylinder extends and retracts within the channel member, the arm moves with respect to the channel member between the upper and lower ends and carries the mounting plate and the probe vertically within the frame between the two collars.

The probe has a front face diameter of between 9 and 12 mm and comprises or is constructed with a piezoelectric material, preferably a copolymer such as for example polyvinylidenefluoride (PVDF) which is a versatile engineering plastic. It is intended that probes for use in the present invention are marinised using known techniques to facilitate their use subsea in depths of up to 3000 m.

The probe comprises an ultrasonic transducer element (not shown) for emitting an ultrasonic beam to a flexible riser and for receiving echoes of the ultrasonic beam reflected from the riser which echo signals can then be converted into an image signal as described below. It is envisaged that the single transducer element may be replaced with a phased array of elements which are fired consecutively to produce a signal over a wider area.

Driving means (not shown) are provided on the frame and coupled to the ultrasonic transducer elements for driving the transducer elements for generating the ultrasonic beam. The driving means are adapted to drive the probe at a voltage of around 700V to 1 Kv such that the probe produces short pulses of between 4 and 6 MHz frequency and a focal length of between 5 and 100 mm.

A control pack 26 is mounted on the frame and includes known means for converting the reflected signals into image signals which can then be viewed at a display means as will be described further below.

Means 27 are provided on the mounting plate and the arm of the frame for moving the mounting plate laterally with respect to the arm. The mounting plate can be moved with respect to the arm to allow the probe to be moved both horizontally and vertically with respect to the frame. The means may for example be a rack and pinion arrangement.

A sensor 28 is mounted within each collar on a rod 29 which extends outwardly from the channel member between the pivotal arms of the collar as will be described further below.

In the illustrated embodiment a single probe is mounted on the frame although multiple probes may be provided as is described further below.

The frame is adapted to be deployed by a remotely operated vehicle (ROV) from a platform or vessel into seawater surrounding the riser and mounting means (not shown) are provided on the frame to facilitate connection and operation by the ROV.

An umbilical 30 is connected between the control means on the frame and a display device (not shown) on the vessel or platform from which the frame is deployed and the umbilical carries the converted image signals to the display means where they can be viewed by an operator of the apparatus.

The method of scanning the flexible riser will now be described.

The frame 11 is prepared on board a vessel or on a platform in the vicinity of the riser to be assessed. The probe 22 is mounted into the frame on the mounting plate 23 and the frame is mounted onto the ROV. The umbilical 30 is connected between the control package 26 and the display means. The arms 16 of the collars are set in the open condition. The ROV is then deployed from the vessel or platform into the water surrounding the riser and the ROV is flown to the appropriate location adjacent the section of the riser to be scanned paying out the umbilical as it goes.

When the ROV reaches the desired position, the frame, with the arms of the collars in the open position, is presented to the riser and the ROV moves the frame into position. As the outer surface of the riser comes into contact with the sensors 28 extending into the frame, the arms 16 of the collars are pivoted into the closed position and the gripping means 17 contact the outer surface of the riser. At this point a signal may be generated by further sensors on the arms to automatically halt the movement of the arms or the operation may be halted by the operator from a remote location. For example a camera may be mounted on the frame to facilitate close control of the arms. The frame can be used to service risers of different diameters as the arms are closed around the outer surface of the riser and can be set at different positions to accommodate different diameters of risers.

The operator then passes a control signal to the frame 11 and the hydraulic cylinder 24 is moved vertically within the channel member 12 to move the probe and therefore the ultrasonic beam emitted from the probe vertically along the outer surface of the riser. As the probe is driven to such a high voltage, the ultrasonic beam generated can assimilate the characteristics of the outer sheath polymer of the riser and penetrate the armour wires thus improving the strength of the resulting reflected signals and providing improved accuracy in the converted image signals that are generated. These signals representing a visual image of the front and back surface of the armour wires and the level or extent of any flooding in the riser determined by locating interfaces between fluid filled sections of the annulus and those sections without fluid are passed along the umbilical 30 and back to the display device on the vessel or platform where they can be viewed and analysed by the operator.

The operator also controls the horizontal movement of the probe relative to the frame by driving the mounting plate 23 over the arm 25 of the frame. As the mounting plate is curved, any movement of the mounting plate horizontally with respect to the channel member keeps the probe at a fixed distance from the outer surface of the riser.

Once the scan is complete in the section covered by the frame, a signal can be passed from the operator to the frame to pivot the arms into the open position thereby releasing the frame 11 from the riser. The frame can then be recovered by the ROV back to the surface or alternatively the ROV can be operated to move the frame to another section of the riser where a further scanning operation can be carried out.

It will be appreciated that the method and apparatus of the present invention provides for real time assessment of the condition of the annulus of a riser and particularly a flexible riser and real time inspection of the armour wire thickness which allows the operator to take remedial action where necessary to address any issues which are identified.

It is to be appreciated that modifications to the invention may be made such as for example in a non illustrated embodiment multiple probes may be mounted within the frame and multiple ultrasonic beams moved over the surface of the riser. For example two pairs of probes may be provided, each mounted at 90 degrees to the next around the frame such that each opposing pair of probes fire ultrasonic beams along the same longitudinal axis. By providing two off set pairs of probes as described, two perpendicular ultrasonic beams can be fired at the riser to provide for a self centering operation of the frame and or the probes.

It will be appreciated that whilst the apparatus described above is intended to be mounted on a riser and the probe or probes moved to scan the ultrasonic beam(s) over the surface of the riser, means may be provided on the frame to facilitate movement of the frame along the riser when the frame is in the closed position. It will be further appreciated that the driving means for moving the frame along the riser may be controlled remotely by the operator by incorporating known control equipment either on the frame or on the ROV. This would enable the frame to complete a scan of a riser without having to be removed and repositioned along the length of the riser.

The embodiments if the apparatus have been described above as used in monitoring the condition of a flexible pipeline, however the apparatus as described may equally be used in relation to other tubular members including rigid pipes and pipelines or risers.

Such rigid pipes may for example be formed of or comprise steel and may have a polymer sheath or coating applied to the surface of the pipe. This polymer sheath or coating provides corrosion protection and or insulation for the pipe.

The invention claimed is:

1. An apparatus for assessing a condition of an annulus of a flexible pipe, the apparatus comprising:
   an ultrasonic probe;
   an ultrasonic transducer element that drives the ultrasonic probe to fire a short pulse ultrasonic beam at an external sheath of the flexible pipe;
   a control pack that converts reflected ultrasonic beam into image signals, the image signals including front and back walls of the flexible pipe; and which can be analysed to assess the condition of the flexible pipe; and
   wherein at least one of natural frequencies and mechanical behaviors of materials of the ultrasonic probe and the external sheath of the flexible pipe are matched.

2. The apparatus according to claim 1 comprising a display that displays the image signals.

3. The apparatus according to claim 2 wherein an umbilical is provided between the probe or probes and the display device.

4. The apparatus according to claim 1, wherein the ultrasonic probe is adapted to be driven at a voltage of around 700V to 1 Kv.

5. The apparatus according to claim 1, wherein the probe fires pulses of between 4 and 6 Mhz with a focal length of between 5 and 100 mm.

6. The apparatus according to claim 1, comprising a frame adapted to be mounted adjacent to or around an outer surface of the flexible pipe.

7. The apparatus according to claim 6 wherein the ultrasonic probe is mounted upon the frame in an orientation perpendicular to a longitudinal axis of the frame.

8. The apparatus according to claim 6 comprising a rack and pinion for moving the frame relative to the flexible pipe.

9. The apparatus according to claim 6 comprising a rack and pinion for moving the frame along or across the outer surface of the flexible pipe.

10. The apparatus according to claim 6 wherein the frame comprises a hinged collar which can open to allow the frame to be mounted around a flexible pipe.

11. The apparatus according to claim 6 wherein means are provided on the frame for moving the probe or probes vertically and/or horizontally over a surface of the flexible pipe.

12. The apparatus according to claim 1 wherein the apparatus further comprises a plurality of probes.

13. The apparatus according to claim 12 wherein the apparatus comprises a pair of probes mounted in a frame in opposing diametric alignment.

14. The apparatus according to claim 13 wherein a second pair of probes is provided perpendicularly to the first pair such that a longitudinal axes of the two pairs of probes cross within the flexible pipe when the frame is mounted on a flexible pipe and the ultrasonic beams fired by the probes converge on a centre of the flexible pipe.

15. The apparatus according to claim 14 comprising a collar of the frame.

16. The apparatus according to claim 1 wherein the probe has a front face diameter of between 9 and 12 mm.

17. The apparatus according to claim 1 wherein the probe comprises polyvinylidenefluoride (PVDF).

\* \* \* \* \*